United States Patent
Shinoda et al.

(10) Patent No.: US 6,939,646 B2
(45) Date of Patent: Sep. 6, 2005

(54) POLYMER ELECTROLYTE AND PROCESS FOR PRODUCING THE SAME

(75) Inventors: Hiroshi Shinoda, Tsukuba (JP); Katsuhiko Iwasaki, Tsukuba (JP); Atsushi Terahara, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 386 days.

(21) Appl. No.: 10/108,441

(22) Filed: Mar. 29, 2002

(65) Prior Publication Data

US 2002/0187377 A1 Dec. 12, 2002

(30) Foreign Application Priority Data

Apr. 4, 2001 (JP) .................................... 2001-105596
Sep. 27, 2001 (JP) .................................... 2001-297814
Dec. 11, 2001 (JP) .................................... 2001-376904

(51) Int. Cl.⁷ .............................................. H01M 6/18
(52) U.S. Cl. ........................ 429/314; 429/315; 429/30; 429/33; 204/296; 521/27
(58) Field of Search ................................ 429/314, 315, 429/30, 33; 204/296; 521/27

(56) References Cited

FOREIGN PATENT DOCUMENTS

| FR | WO 9905126 | * | 2/1999 |
| JP | 2000-188013 A | | 7/2000 |
| WO | WO 99/61141 A1 | | 12/1999 |

* cited by examiner

*Primary Examiner*—Bruce F. Bell
(74) *Attorney, Agent, or Firm*—Sughrue Mion, PLLC

(57) ABSTRACT

A polymer electrolyte having, in a main chain, a structural unit represented by the following formula (1):

$$-[Ar^1-(SO_2-N^-(X^+)-SO_2-Ar^2)_m-SO_2-N^-(X^+)-SO_2-Ar^1-O]- \qquad (1)$$

wherein $Ar^1$ and $Ar^2$ independently represent a divalent aromatic groups, m represents an integer of 0 to 3, and $X^+$ represents an ion selected from hydrogen ion, an alkali metal ion and ammonium ion, which is excellent in proton conductivity, thermal resistance and strength. The polymer electrolyte is soluble in solvents and has excellent film forming property and recycling efficiency.

23 Claims, No Drawings

POLYMER ELECTROLYTE AND PROCESS FOR PRODUCING THE SAME

BACKGROUND OF THE INVENTION

1. Field of the Invention

The present invention relates to a polymer electrolyte, in particular a polymer electrolyte suitably used as a separator in electrochemical devices such as batteries, fuel cells and the like, and to a process for producing the same.

2. Description of the Related Art

Polymer electrolytes having ion-conducting property have been used as separators in electrochemical devices such as primary cells, secondary cells, solid polymer type fuel cells and the like. Polymer materials having an acidic group such as sulfonic acid group, carboxylic acid group, phosphoric acid group and the like or a metal salt thereof are used as such polymer electrolytes.

For example, in the solid polymer type fuel cells, polymer electrolytes of perfluorosulfonic acid type including Nafion (trademark, E. I. DuPont de Nemours Co.) have been used as the polymer electrolytes having ion-conducting property. Since, however, these electrolytes had a problem that they were low in the membrane strength, thermal resistance and so on. While sulfonated products of random copolymers obtained from 4,4'-dihydroxydiphenylsulfone, 4,4'-dihydroxybiphenyl and 4,4'-dichlorodiphenylsulfone have also been proposed, their proton conductivity is not necessarily sufficient for satisfaction and polymer electrolytes having a higher proton conductivity have been demanded.

On the other hand, compounds having disulfonylimide units in the cross-linking moieties have been known as polymer electrolytes having a disulfonylimide unit. For example, polymer electrolytes formed by cross-linking perfluoro-type sulfonyl fluoride membrane with perfluorobutane-1,4-disulfonamide (JP-A-2000-188013), polymer electrolytes formed by cross-linking chlorosulfonated polyether-ether ketone with 2,5-dichlorobenzene-1, 4-disulfonamide (WO 99/61141) and the like have been proposed. Since these cross-linked polymer electrolyte membranes are insoluble and infusible, there has been a fear that recovery and reuse of materials become very difficult due to difficult separation thereof from electrode materials when they are used as separators in cells. In addition, since a step of cross-linkage is necessary after membrane molding, there is a problem that the process for production becomes complicated.

SUMMARY OF THE INVENTION

Under these circumstances, the present inventors have conducted extensive studies on polymer compounds having a disulfonylimide unit. As the result, they have found the facts that polymer compounds having a specific disulfonylimide unit, i.e. bis(arylsulfonyl)imide, in a main chain have a characteristic as the polymer electrolyte, are excellent in thermal resistance, can be easily formed membranes, and can be recovered as a material so that they have a good possibility for recycling, and additionally, the fact that said polymer compounds keep a high ion-conducting property when they are formed as a composite membrane with a porous membrane.

Accordingly, the present invention provides [1] a polymer electrolyte, which is excellent in practical use, having, in a main chain, a structural unit represented by the following formula (1):

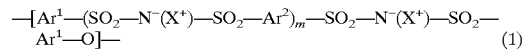

$$-[Ar^1-(SO_2-N^-(X^+)-SO_2-Ar^2)_m-SO_2-N^-(X^+)-SO_2-Ar^1-O]- \quad (1)$$

wherein $Ar^1$ and $Ar^2$ independently represent divalent aromatic groups, m represents an integer of 0 to 3, and $X^+$ represents an ion selected from hydrogen ion, an alkali metal ion and ammonium ion.

The invention also provides [2] the polymer electrolyte of the above [1], further having, in a main chain, a structural unit represented by the following formula (2):

$$-[Ar^3-O]- \quad (2)$$

wherein $Ar^3$ represents a divalent aromatic group.

The invention provides [3] the polymer electrolyte of the above [2], further having, in a main chain, a structural unit represented by the following formula (2') which is different from the formula (2);

$$-[Ar^4-O]- \quad (2')$$

wherein $Ar^4$ represents a divalent aromatic group.

The invention further provides [4] a composite membrane comprising a polymer electrolyte of the above [1], [2] or [3], and a porous membrane, which is excellent in practical use.

DETAILED DESCRIPTION OF THE INVENTION $Ar^1$ and $Ar^2$ in the above formula (1) independently represent a divalent aromatic group. Examples of the divalent aromatic groups include the following groups.

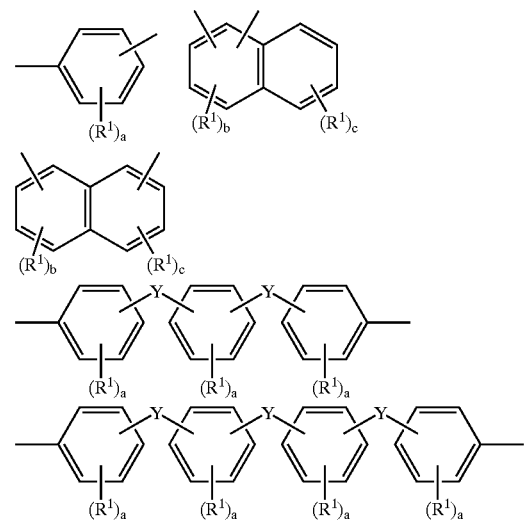

wherein $R^1$ represents alkyl having 1 to 10 carbon atoms, alkoxy having 1 to 10 carbon atoms, halogenated alkyl having 1 to 10 carbon atoms, aryl, acetyl, benzoyl, nitrile, sulfonic acid, a carboxylic acid, phosphonic acid or halogen; a represents an integer of 0 to 4; b and c represent integers of 0 to 4, with the sum of b and c being an integer of 0 to 6; when a plurality of $R^1$s exist, they may be the same or different; Y represents a direct bond, —O—, —S—, —C(O)—, —SO$_2$— or —C(R$^3$)$_2$— wherein $R^3$ represents hydrogen, alkyl having 1 to 10 carbon atoms or halogenated alkyl having 1 to 10 carbon atoms, aryl, with the two $R^3$s being possible to be the same or different or to form a ring; and when a plurality of Ys exist, they may be the same or different.

Examples of alkyl having 1 to 10 carbon atoms include methyl, ethyl, propyl, phenyl, naphthyl and the like.

Examples of alkoxy having 1 to 10 carbon atoms include methoxy, ethoxy, and the like. Halogenated alkyl having 1 to 10 carbon atoms include trifluoromethyl, pentafluoroethyl, and the like. Examples of aryl include phenyl, naphthyl, phenoxy and the like. Examples of halogen include fluorine, chlorine and bromine.

Examples of halogenated alkyl having 1 to 10 carbon atoms for $R^3$ include trifluoromethyl and the like. Examples of the ring formed by two $R^3$s include cyclohexane ring, fluorene ring and the like.

The degree of ionic dissociation for sulfonylimide group varies depending on substituents on the adjacent aromatic groups $Ar^1$ and $Ar^2$, and the degree of ionic dissociation increases with increasing electron attracting property of the substituent. Therefore, compounds having a substituent of higher electron attracting property as $Ar^1$ and $Ar^2$, for example those having a halogen atom as a substituent, are preferred, and those having a fluorine atom as a substituent are more preferred. In particular, compounds wherein $Ar^1$ or $Ar^2$ are tertrafluorophenylene are particularly preferred because the degree of ionic dissociation for disulfonylimide group in this case is higher.

$X^+$ includes hydrogen ion, an alkali metal ion and ammonium ion. When the polymer electrolyte is used in fuel cells, $X^+$ is preferably hydrogen ion.

The polymer electrolyte of the invention is characterized in that it has a structural unit represented by the formula (1) as described above in the main chain. But usually the electrolyte has this structural unit together with another structural unit, and it may be an alternating copolymer, a random copolymer or a block copolymer.

Examples of preferred structural unit other than the structural unit represented by the formula (1) include structural unit s represented by the formula (2), shown below, and the like. In addition to the structural unit of the formula (2), the electrolyte may have a structural unit different from this structural unit. Examples of such structural unit include structural units represented by the formula (2'), without particular limitation.

$$—[Ar^3—O]— \quad (2)$$

$$—[Ar^4—O]— \quad (2')$$

wherein $Ar^3$ and $Ar^4$ independently represent a divalent aromatic group. The divalent aromatic group is has usually 6 to 24 carbon atoms, preferably 6 to 18 carbon atoms, and may have a substituent, such as methyl, ethyl, sulfonic acid group, etc.

Examples of the divalent aromatic groups include the groups as the same with $Ar^1$ and $Ar^2$ as described above.

The polymer electrolyte having structural units represented by the above formulae (1) and (2) can be produced, for example, by using a compound represented by the formula (3) shown below, an aromatic diol represented by the formula (4) shown below or the like and polymerizing them.

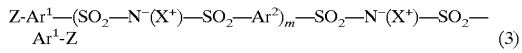

$$Z-Ar^1—(SO_2—N^-(X^+)—SO_2—Ar^2)_m—SO_2—N^-(X^+)—SO_2—Ar^1-Z \quad (3)$$

$$HO—Ar^3—OH \quad (4)$$

wherein $Ar^1$, $Ar^2$, $Ar^3$, m and $X^+$ represent the same meanings as above formula (1); and Z represents halogen or nitro.

Examples of halogen here include fluorine, chlorine, bromine and the like. Preferred examples are fluorine and chlorine, with fluorine being more preferred.

Typical examples of the aromatic diol represented by formula (4) include hydroquinone, resorcinol, catechol, 2-methylhydroquinone, 2,6-dimethylhydroquinone, 2-methoxyhydroquinone, 2-phenylhydroquinone, 2,6-diphenylhydroquinone, 2-sulfohydroquinone, 2,6-disulfohydroquinone, 2-methylresorcinol, 2,4-dimethylresorcinol, 2-phenylresorcinol, 2,4-diphenylresorcinol, 1,2-dihydroxynaphthalene, 1,4-dihydroxynaphthalene, 1,5-dihydroxynaphthalene, 2,6-dihydroxynaphthalene, 2,7-dihydroxynaphthalene, 6,7-dihydroxy-2-naphthalenesulfonic acid, 2,7-dihydroxynaphthalene-3,6-disulfonic acid, 4,5-dihydroxynaphthalene-2,7-disulfonic acid, 4,4'-dihydroxybiphenyl, 4,4'-dihydroxy-3,3'-disulfobiphenyl, 4,4'-dihydroxy-3,3'-diphenylbiphenyl, 2,4'-dihydroxybiphenyl, 2,2'-dihydroxybiphenyl, 4,4'-dihydroxydiphenylmethane, 1,1-bis(4-hydroxyphenyl)ethane, 2,2-bis(4-hydroxyphenyl)propane, 2,2-bis(4-hydroxyphenyl)butane, 1,1-bis(4-hydroxyphenyl)cyclohexane, 2,2-bis(4-hydroxyphenyl)-1,1,1,3,3,3-hexafluoropropane, 1,1-bis(4-hydroxyphenyl)-1-phenylethane. bis(4-hydroxyphenyl)diphenylmethane, 9,9-bis(4-hydroxyphenyl)fluorene, 4,4'-dihydroxydiphenylether, bis(4-hydroxyphenyl)sulfide, bis(3,5-dimethyl-4-hydroxyphenyl)sulfide, 4,4'-dihydroxybenzophenone, 4,4'-dihydroxydiphenylsulfone, 4,4'-dihydroxy-3,3'-disulfodipheanylsulfone, bis(3,5-dimethyl-4-hydroxyphenyl)sulfone, alkali metal salts (sodium salt, potassium salt) of them and the like. Two or more of them can be used.

Amongst preferred are hydroquinone, 4,4'-dihydroxybiphenyl, 2,2-bis(4-hydroxyphenyl)propane, 4,4'-dihydroxy-3,3'-diphenylbiphenyl, 4,4'-dihydroxydiphenylether, alkali metal salts of them and the like, because of their high reactivity.

The compound represented by the formula (3) as the other raw material can be produced in the following manner.

The compounds wherein m is 0 can easily be produced, for example, by reacting $Z-Ar^1—SO_2Cl$ which is the corresponding sulfonyl chloride compound with $Z-Ar^1—SO_2NH_2$ which is the corresponding sulfonamide compound. Usually, the reaction is carried out in a solvent adjusting the pH value in the system to 7 to 8 and with addition of 2 times the equivalent or more of a base.

Examples of the solvent include acetone, 2-butanone, tetrahydrofuran, 1,4-dioxane, acetonitrile, N,N-dimethylacetamide, N,N-dimethylformamide, dimethylsulfoxide, a mixture of two or more of them and the like. Usable base includes sodium hydride, lithium hydride, triethylamine, pyridine, dimethylaminopyridine and the like. The reaction temperature is preferably about 0° C. to 150° C. and more preferably 20° C. to 80° C. The reaction period is usually about 1 hour to 20 hours.

The sulfonamide compound used here can be produced, for example, by reacting $Z-Ar^1—SO_2Cl$ which is the corresponding sulfonyl chloride compound with ammonia, ammonium chloride or the like in the presence of two times the equivalent or more of a base.

Among the compound represented by the formula (3), the compound wherein m is 1 can easily be produced, for example, by reacting $Z-Ar^1—SO_2NH_2$ which is the sulfonamide compound with $ClSO_2—Ar^2—SO_2Cl$ which is the corresponding bissulfonyl chloride compound, or by reacting $Z-Ar^1—SO_2Cl$ which is the sulfonyl chloride compound with $NH_2SO_2—Ar^2—SO_2NH_2$ which is the corresponding bissulfonamide compound The reaction is carried out, for example, under conditions similar to those for the compound wherein m is 0. The bissulfonamide compound used here can also be produced, for example, by reacting the corresponding bissulfonyl chloride compound with ammonia, ammonium chloride or the like.

Among the compound represented by the formula (3), the compound wherein m is 2 or 3 can be produced, for example, by reacting the bissulfonyl chloride compound and the bissulfonamide compound with the sulfonyl chloride compound or the sulfonamide compound in a ternary system. The length of oligomer chain can be adjusted by the molar ratio of compounds. However, since increase in the molecular weight of the final polymer is sometimes difficult because of difficulty in purification at the stage of the compound (3) due to the distribution in chain length, it is preferred to use the compound (3) wherein m is 0 or m is 1.

Typical examples of the sulfonyl chloride compound used for the production of the compound (3) include 4-fluorobenzenesulfonyl chloride, 3-fluorobenzenesulfonyl chloride, 2-fluorobenzenesulfonyl chloride. difluorobenzenesulfonyl chloride, trifluorobenzenesulfonyl chloride, tetrafluorobenzenesulfonyl chloride, pentafluorobenzenesulfonyl chloride, 4-chlorobenzenesulfonyl chloride, 3-chlorobenzenesulfonyl chloride, 2-chlorobenzenesulfonyl chloride, dichlorobenzenesulfonyl chloride, trichlorobenzenesulfonyl chloride, 4-bromobenzenesulfonyl chloride, 3-bromobenzenesulfonyl chloride, 2-bromobenzenesulfonyl chloride, dibromobenzenesulfonyl chloride, 4-nitrobenzenesulfonyl chloride, 3-nitrobenzenesulfonyl chloride and the like. Two or more of them can be used. In addition, sulfonyl fluoride compounds can be used in place of these sulfonyl chloride compounds.

Typical examples of the bissulfonyl chloride compound used for the production of the compound (3) include 1,4-benzenedisulfonyl chloride, 1,3-benzenedisulfonyl chloride, 1,2-benzenedisulfonyl chloride, 4,4'-biphenyldisulfonyl chloride, naphthalenedisulfonyl chloride and the like. Two or more of them can be used. In addition, bissulfonyl fluoride compounds can be used in place of these bissulfonyl chloride compounds.

The polymer electrolyte of the invention can be produced by using a compound represented by the formula (3), an aromatic diol represented by the formula (4) or the like, described above, as the raw materials and polymerizing them. Specific process for the production is not particularly limited and includes for example, [1] a process in which a compound represented by the above formula (3) and an aromatic diol represented by the above formula (4) are reacted; [2] a process in which a compound represented by the above formula (3), an aromatic diol represented by the above formula (4) and a compound represented by the formula (5) shown below are reacted; [3] a process in which a compound represented by the above formula (3) and an aromatic diol represented by the above formula (4) are reacted, followed by the reaction with a compound having a hydroxyl group represented by the formula (6) shown below; [4] a process in which a compound represented by the above formula (3) and an aromatic diol represented by the above formula (4) are reacted, followed by the reaction with a compound represented by the formula (7) shown below; [5] a process in which a compound represented by the above formula (3) and an aromatic diol represented by the above formula (4) are reacted, followed by the reaction with a compound represented by the formula (5) shown below and a compound having a hydroxyl group represented by the formula (6) shown below; [6] a process in which a compound represented by the above formula (3) and an aromatic diol represented by the above formula (4) are reacted, followed by the reaction with an aromatic diol represented by the above formula (4) and a compound represented by the formula (7) shown below; and the like, in the presence of an alkali.

$$W\text{-}Ar^4\text{-}W \quad (5)$$

$$HO\text{—}[Ar^5\text{—}O]_j\text{—}H \quad (6)$$

$$W\text{-}[Ar^6\text{—}O]_j\text{—}Ar^6\text{-}W \quad (7)$$

wherein $Ar^4$ represents the same meanings as above; $Ar^5$ and $Ar^6$ independently represent a divalent aromatic group; and W represents halogen or nitro; and j represents an integer of 1 to 5000. The divalent aromatic group is has usually 6 to 24 carbon atoms, preferably 6 to 18 carbon atoms, and may have a substituent, such as methyl, phenyl, halogen, etc. Examples of halogen include fluorine, chlorine, bromine and the like.

Examples of halogen (W) used in formula (5) or (7) include fluorine, chlorine, bromine and the like.

Typical examples of the compound represented by the formula (5) include 4,4'-difluorobenzophenone, 4,4'-dichlorobenzophenone, 2,4-difluorobenzophenone, 4,41-dibromobenzophenone, 3,4'-dinitrobenzophenone, 4,4'-difluorodiphenylsulfone, 4,4'-difluoro-3,3'-disulfodiphenylsulfone, dipotassium salt of 4,4'-difluoro-3,3'-disulfodiphenylsulfone, disodium salt of 4,4'-difluoro-3,3'-disulfodiphenylsulfone, 4,4'-dichlorodiphenylsulfone, 4,4'-dichloro-3,3'-disulfodiphenylsulfone, dipotassium salt of 4,4'-dichloro-3,3'-disulfodiphenylsulfone, disodium salt of 4,4'-dichloro-3,3'-disulfodiphenylsulfone, 4,4'-dibromodiphenylsulfone, 4,4'-dinitrodiphenylsulfone, 2,6-difluorobenzonitrile, 2,6-dichlorobenzonitrile, hexafluorobenzene, decafluorobiphenyl, octafluoronaphthalene and the like. Two or more of them can be used.

Amongst them, 4,4'-difluorobenzophenone, 4,4'-difluorodiphenylsulfone, 4,4'-dichlorodiphenylsulfone, decafluorobiphenyl and the like are preferred.

Examples of $Ar^5$ in the compound having a hydroxyl group represented by the formula (6) include the same divalent aromatic group as described above. $Ar^5$ may be the same as or be different from $Ar^3$, $Ar^4$ and the like. Examples of the compound (6) having a hydroxyl group are not particularly limited and include aromatic polymers such as polyphenylene ethers, polyether ketones, polyether-ether ketones, polysulfones, polyether sulfones, polyphenylene sulfides and the like having a hydroxyl group at their terminal. Two or more of them can be used.

Examples of $Ar^6$ in the compound represented by the formula (7) include the same divalent aromatic group as described above. $Ar^6$ may be the same as or be different from $Ar^3$, $Ar^4$, $Ar^5$ and the like. Examples of such compound (7) are not particularly limited and include aromatic polymers such as polyphenylene ethers, polyether ketones, polyether-ether ketones, polysulfones, polyether sulfones, polyphenylene sulfides and the like having a halogen or a nitro group at their terminal. Two or more of them can be used together.

The number average molecular weight of the compounds (6) and (7) described above is preferably 2,000 to 500,000, more preferably 5,000 to 200,000, and most preferably 8,000 to 100,000. When the number average molecular weight is smaller than 2,000, sometimes the membrane strength or thermal resistance of the block copolymer becomes lowered, and when the number average molecular weight is more than 500,000, sometimes the solubility becomes lowered.

The polymerization reaction can be carried out according to a known process in which the reaction is realized in the co-presence of an alkali. Any known alkali having a polymerization activity can be used as the alkali here. Preferably used alkalis include alkali metal hydroxides, alkali metal carbonates and the like. Among them, potassium carbonate is preferred.

In addition, while the polymerization reaction may be carried out in a molten state without solvent, the reaction preferably carried out in a solvent. Usable solvents include aromatic hydrocarbon solvents, ether solvents, ketone solvents, amide solvents, sulfone solvents, sulfoxide solvents and the like, with dimethylsulfoxide, sulfolane, N,N-dimethylformamide, N,N-dimethylacetamide, N-methylpyrrolidone, N,N'-dimethylimidazolidinone, diphenylsulfone and the like being preferred.

The reaction temperature for the polymerization reaction is usually 20° C. to 300° C., preferably 50° C. to 200° C. In view of the heat resistance and strength of the film, the number average molecular weight of the polymer is preferably 5000 to 1000000, and more preferably 10000 to 500000.

The polymer electrolyte can be taken out, for example, by adding dropwise the reaction solution after completion of the reaction into a non-solvent for the polymer to form precipitates, which are filtered or decanted. Examples of the non-solvent include methanol, water, hydrochloric acid, diethyl ether, acetone and the like. They can be used independently, and in a mixture of two or more, if necessary. Particularly preferred are water, methanol, a mixture of hydrochloric acid and methanol, a mixture of hydrochloric acid and water, and the like.

In addition, a substituent can be introduced on an aromatic ring after the polymerization. For example, sulfonic acid group can be introduced by reacting the obtained polymer electrolyte with concentrated sulfuric acid, fuming sulfuric acid, chlorosulfonic acid or the like.

The polymer electrolytes of the invention having the structural units represented by the formulae (1) in the main chain are produced in the above manner, and when the polymer electrolytes of the invention are used as a separator in electrochemical devices such as lithium cell, fuel cell and the like, they are usually used in the form of films. Processes for transforming the polymer electrolytes of the invention into films are not particularly limited and a process in which a film is produced from a solution (solvent casting process) is preferred.

Specific examples of the solvent casting process include a process in which a polymer electrolyte is dissolved in an appropriate solvent, the solution is tasted by applying it on a glass plate, a Teflon plate or the like, and removing the solvent with heating under reduced pressure, if necessary, to form a membrane.

The solvents used for the production of membranes are not particularly limited as far as they can dissolve the polymer electrolyte and can be removed thereafter, and preferred examples include aprotic polar solvents such as N,N-dimethylformamide, N,N-dimethylacetamide, N-methyl-2-pyrrolidone, dimethylsulfoxide and the like; chlorinated solvents such as dichloromethane, chloroform, 1,2-dichloroethane, chlorobenzene, dichlorobenzene and the like; alcohols such as methanol, ethanol, propanol and the like; and alkylene glycol monoalkyl ethers such as ethylene glycol monomethyl ether, ethylene glycol monoethyl ether, propylene glycol monomethyl ether, propylene glycolmonoethyl ether and the like. They can be used independently, and in a mixture of two or more, if necessary. Particularly preferred among them are N,N-dimethylformamide, N,N-dimethylacetamide, N-methylpyrrolidone, dimethylsulfoxide, a mixed solvent of methylene chloride and methanol and the like, because of their high solubility for the polymer electrolytes.

The thickness of films is not particularly limited and preferably 10 to 200 $\mu$m, more preferably 20 to 150 $\mu$m. When the film has a thickness less than 10 $\mu$m, the practical strength is not sufficient, sometimes. When the film has a thickness greater than 200 $\mu$m, the film has a tendency to a too greater membrane resistance causing insufficient properties of electrochemical devices. The membrane thickness can be controlled by the concentration of the polymer electrolyte solution and the thickness of the coating on substrate.

In addition, any solvents, salts or the like contained in the membrane can be removed by washing the membrane obtained in the above manner with, for example, ion-exchange water. An electrolyte membrane of the formula (1) wherein $X^+$ is $H^+$ is obtained by immersing the membrane in hydrochloric acid and then washing it with ion-exchange water.

The ion exchange capacity of the polymer electrolyte (molar number of acidic group per 1 g of the polymer electrolyte) is preferably 0.5 meq/g to 3.0 meq/g and more preferably 0.8 meq/g to 1.8 meq/g. When the ion exchange capacity is less than 0.5 meq/g, sometimes a sufficient ion-conducting property cannot be obtained and the performance as a polymer electrolyte is lowered. When the ion exchange capacity is greater than 3.0 meq/g, sometimes the water resistance is lowered.

Furthermore, in the present invention, a plasticizer, stabilizer, release agent or the like usually used in the polymer can be added to the polymer electrolyte of the invention for the purpose of improvement in various physical properties of the film. In addition, it is also possible to make a complex alloy of the polymer electrolyte with another polymer by the mixed co-casting process in the same solvent or other processes. In particular, co-use of an aromatic polyimide is preferred and, by such a co-use, the film strength, water resistance or the like can be improved.

Methods containing addition of a low molecular electrolyte, an acid compound, or another polymer electrolyte, and impregnation of a solvent or else have been known for the purpose of improving the ion-conducting property or others. Furthermore, in the fuel cell use, in order to make easy the water control, addition of inorganic or organic fine particles is known as the water retention agent. All these known techniques can also be used as far as the purpose of the invention is not damaged.

Additionally, in the present invention, the product can be cross-linked by irradiating an electron beam, radiation or the like for the purpose of improvement in the mechanical strength of the film. Furthermore, reinforcement of the film is known by impregnating the porous film or sheet (porous membrane) to form a composite material or by mixing a fiber or pulp. All these known techniques can also be used as far as the purpose of the invention is not damaged.

Since the porous membrane is used in order to further improvement in the strength, flexibility and durability, any membrane can be used as far as it meets the purpose of use irrespective of its shape and material. When it is used as a separator in the solid polymer type fuel cell, the membrane thickness is usually 1 to 100 $\mu$m, preferably 3 to 30 $\mu$m, more preferably 5 to 20 $\mu$m, the pore diameter is usually 0.01 to 10 $\mu$m, preferably 0.02 to 7 $\mu$m, and the porosity is usually 20 to 98%, preferably 30 to 95%. The material for the porous membrane is preferably an aliphatic polymer or a fluorine-containing polymer, from the viewpoint of thermal resistance and in view of reinforcing effect on the mechanical strength.

Examples of the aliphatic polymer include polyethylene, polypropylene, ethylene-propylene copolymer and the like. The polyethylene referred to here means an ethylene polymer having a polyethylene crystal structure and includes, for example, a copolymer of ethylene and another monomer. Specifically included is a copolymer of ethylene and an α-olefin, called linear low density polyethylene (LLDPE). The polypropylene referred to here means a propylene polymer having a polypropylene crystal structure and includes generally used propylene block copolymers, random copolymers and the like (which are copolymers with ethylene and 1-butene).

As the fluorine-containing porous membrane, any thermoplastic resins having at least one carbon-fluorine bond in the molecule can be used without limitation. Usually, resins having a structure in which all or most of hydrogen atoms in the aliphatic polymer is replaced by fluorine atoms are preferably used. Examples include polytrifluoroethylene, polytetrafluoroethylene, polychlorotrifluoroethylene, poly(tetrafluoroethylene-hexafluoropropylene), poly(tetrafluoroethylene-perfluoroalkyl ether), polyvinylidene fluoride and the like. Among then, polytetrafluoroethylene and poly(tetrafluoroethylene-hexafluoropropylene) are preferred, with polytetrafluoroethylene being particularly preferred. These fluorine resins preferably have an average molecular weight of 100,000 or more, in view of their good mechanical strength.

Methods for making a composite material with a porous membrane are not particularly limited. Examples include a method in which a porous membrane is immersed in a solution of a polymer electrolyte, taken out and then freed from the solvent to give a composite membrane; a method in which a solution of a polymer electrolyte is applied onto a porous membrane and then freed from the solvent to give a composite membrane; a method in which a porous membrane is brought into contact with a solution of a polymer electrolyte under reduced pressure, then the solution is impregnated into pores of the porous membrane by applying the ordinary pressure, and the membrane is freed from the solvent to give a composite membrane; and others.

The fuel cell according to the present invention is described below.

The fuel cell of the invention is obtained by installing, into a cell, a membrane-electrodes assembly comprising an anode and a cathode comprising gas diffusion electrodes containing a catalyst and a polymer electrolyte placed between the anode and the cathode, said assembly being inserted between separators comprising a conductive carbon plate having a groove acting as a conduit for hydrogen gas, air or oxygen gas.

Said catalyst is not particularly limited as far as it can activate the oxidation-reduction reaction of hydrogen or oxygen and may be a known product. Preferred product is fine powders of platinum or fine powders of platinum alloy. Said powders are often carried on a particulate or fibrous carbon such as activated carbon or graphite.

Gas diffusion layers in said gas diffusion electrodes may also be known materials and preferably a porous carbon nonwoven fabric or carbon paper.

Methods for producing a membrane-electrode assembly may be known processes. Examples include a method in which two plates are formed having a gas diffusion layer and a catalyst bound thereto, and a polymer electrolyte membrane is inserted and bound between them; and a method in which a catalyst is bound to a polymer electrolyte membrane and the obtained assembly is inserted and bound between gas diffusion layers.

EXAMPLES

The invention will now be described with reference to Examples, which should not be construed as a limitation upon the invention.

Methods of Measurement (1) 10% Weight Loss Temperature:

Using a thermogravimetric analyzer (TGA-50, manufactured by Shimadzu Corporation), 10% weight loss temperature was measured in the condition of a temperature raising rate of 10° C./min under nitrogen atmosphere.

(2) Molecular Weight (Mn):

Polystyrene-reduced number average molecular weight was measured by GPC (HLC-8020 (manufactured by TOSOH Corporation) equipped with a UV detector (UV-8010 manufactured by TOSOR)) with using a solvent of N,N-dimethylacetamide containing 0.05M LiBr.

(3) Ion Exchange Capacity:

After a polymer electrolyte film was immersed in 0.1N NaOH aqueous solution, neutralization titration of said aqueous solution with 0.1N HCl aqueous solution was conducted, and the value of ion exchange capacity was calculated.

(4) Proton Conductivity:

With using a SI 1260 high performance IMPEDANCE/GAIN-PHASE ANALYZER (manufactured by Solartoron Company) and a 1287 type potentiostat (ELECTROCHEMICAL INTERFACE, manufactured by Solartoron Company), proton conductivity was measured by AC impedance method in a thermo-hygrostat oven at 80° C. and 90% RH.

Synthesis Example 1

Synthesis Example of a Disulfonylimide

To an aqueous solution of ammonium chloride was added dropwise an acetone solution of 1,3-benzenedisulfonyl chloride at room temperature. During addition, pH was adjusted to 7 with an aqueous sodium hydroxide solution. Precipitated product was filtered and recrystallized from ethanol to give 1,3-benzenedisulfonamide. The structure was confirmed by $^1$H-NMR and IR.

Then, 4 times by mole of NaH was added to a tetrahydrofuran solution of 1,3-benzenedisulfonamide. Subsequently, 2 times by mole of pentafluorobenzenesulfonyl chloride was gradually added to the mixture and allowed to react at 60° C. The reaction mass was filtered and the filtrate was concentrated. The residue was dissolved in methanol and combined with a methanol solution of KOH to give the desired sulfonylimide (may be referred to as BSI 1) in the form of potassium salt. The product was recrystallized from a mixed solvent of acetone and methanol.

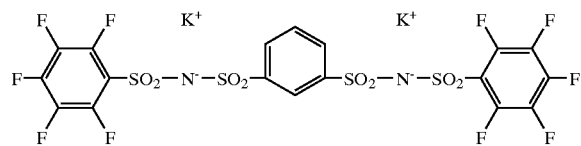

$^1$H-NMR (ppm): 7.52, 7.64, 7.71; $^{19}$F-NMR (ppm): −129, −143, −154.

Example 1

An Alternating Copolymer Comprising BSI 1 and Biphenol

Into a flask were placed 0.500 g of BSI 1, 0.121 g of 4,4'-dihydroxybiphenyl, 94 mg of potassium carbonate and 3 ml of dimethylsulfoxide (hereinafter, referred to as DMSO) under nitrogen stream and they were heated with stirring at 100° C. for 18 hours. The reaction solution was added dropwise to 10% aqueous hydrochloric acid solution. The obtained precipitates were collected by filtration, washed with methanol and then dried under reduced pressure at 60° C. to give 0.48 g of a disulfonylimide polymer in the form of a white solid. The result of molecular weight measurement (converted to polystyrene) is shown in Table 1.

The obtained polymer was dissolved in DMAc to a concentration of about 10% by weight, casted in a glass dish and dried at 80° C. for removing the solvent to give a colorless and transparent tough film having a thickness of 105 μm. The proton conductivity of the film was measured by alternating current method under conditions including a temperature of 80° C. and a humidity of 90%. Additionally, the ion exchange capacity was measured by titration method. The results are collectively shown in Table 1.

Example 2

A Random Copolymer Comprising BSI 1, Bisphenol A and Decafluorobiphenyl

Into a flask were placed 0.773 g of BSI 1, 0.435 g of Bisphenol A, 0.334 g of decafluorobiphenyl, 0.290 g of potassium carbonate and 7.5 ml of DMSO under nitrogen stream and they were heated with stirring at 80° C. for 30 hours. After completion of the reaction, the reaction solution was added dropwise to 10% methanolic hydrochloric acid solution. The obtained precipitates were collected by filtration, washed with methanol and then dried under reduced pressure at 60° C. to give 0.93 g of a disulfonylimide polymer in the form of a pale brown solid. The results of measurement for molecular weight and 10% weight loss temperature are shown in Table 1.

The obtained polymer was converted into a film in the same manner as that in Example 1 to give a transparent and pale brown tough film having a thickness of 36 μm. The results of measurement for proton conductivity and the ion exchange capacity of the film are collectively shown in Table 1.

Example 3

A Block Copolymer Formed by Reacting a Disulfonylimide Oligomer Having Terminal Fluorine Groups and Composed of BSI 1 and Bisphenol A with a Polyether Sulfone Having Terminal Hydroxy Groups A polyether sulfone oligomer (molecular weight Mn: $2.0 \times 10^4$) having terminal hydroxy groups was synthesized by polycondensing 4,4'-dihydroxydiphenylsulfone and 4,4'-dichlorodiphenylsulfone in a molar ratio of 16:15 in diphenylsulfone as the solvent at a temperature of 200 to 290° C.

Into a flask were placed 1.267 g of BSI 1, 0.310 g of Bisphenol A, 0.220 g of potassium carbonate and 6 ml of DMAc under nitrogen stream and they were heated with stirring at 80° C. for 12 hours. Then, 1.00 g of the polyether sulfone oligomer having terminal hydroxy groups synthesized above was added and the reaction was continued at 80° C. for 20 hours. After completion of the reaction, the polymer was recovered in the same manner as that in Example 2 to give 2.01 g of a block copolymer having disulfonylimide blocks in the form of a pale yellow solid. The results of measurement for molecular weight and 10% weight loss temperature are shown in Table 1.

The obtained polymer was converted into a film in the same manner as that in Example 1 to give a semi-transparent and colorless tough film having a thickness of 147 μm. The results of measurement for proton conductivity and the ion exchange capacity of the film are collectively shown in Table 1.

Synthesis Example 2

Synthesis Example of a Disulfonylimide

To an aqueous solution of ammonium chloride was added dropwise an acetone solution of pentafluorobenzenesulfonyl chloride at room temperature. During addition, pH was adjusted to 7 by an aqueous sodium hydroxide solution. Precipitated product was filtered and recrystallized from toluene to give pentafluorobenzenesulfonamide. The structure was confirmed by $^1$H-NMR, $^{19}$F-NMR and IR.

To a tetrahydrofuran solution of pentafluorobenzenesulfonamide was added 2 times by mole of NaH. Subsequently, equimolar of pentafluorobenzenesulfonyl chloride was gradually added to the mixture and allowed to react at 60° C. The reaction mass was filtered and the filtrate was concentrated. The residue was dissolved in methanol and combined with a methanol solution of KOH to give the desired sulfonylimide (may be referred to as BSI 2) in the form of potassium salt. The product was recrystallized from a mixed solvent of acetone and methanol. $^{19}$F-NMR (ppm) −130, −142, −154.

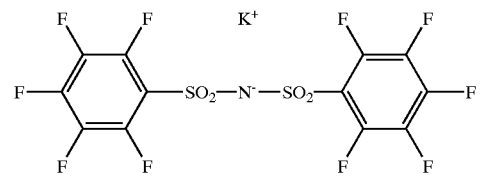

Example 4

An Alternating Copolymer Comprising BSI 2 and Hydroquinone

Into a flask were placed 2.577 g of BSI 2, 0.551 g of hydroquinone, 0.795 g of potassium carbonate and 12 ml of dimethylsulfoxide under nitrogen stream and they were heated with stirring at 80° C. for 19 hours. After completion of the reaction, the polymer was recovered in the same manner as that in Example 2 to give 3.00 g of a disulfonylimide polymer in the form of a brown solid. The results of measurements for molecular weight and 10% weight loss temperature are shown in Table 1.

The obtained polymer was converted into a film in the same manner as that in Example 1 to give a semi-transparent and pale brown tough film having a thickness of 54 μm. The results of measurement for proton conductivity and the ion exchange capacity of the film are collectively shown in Table 1.

Example 5

An Alternating Copolymer Comprising BSI 2 and 4,4'-dihydroxy-3,3'-diphenylbiphenyl Into a flask were placed 2.000 g of BSI 2, 1.313 g of 4,4'-dihydroxy-3,3'-diphenylbiphenyl, 0.563 g of potassium carbonate and 8 ml of dimethylsulfoxide under nitrogen stream and they were heated with stirring at 80° C. for 20 hours. After completion of the reaction, the polymer was recovered in the same manner as that in Example 2 to give 3.00 g of a disulfonylimide polymer in the form of a white solid. The result of measurement for molecular weight and 10% weight loss temperature are shown in Table 1.

The obtained polymer was dissolved in a mixed solvent of methylene chloride and methanol in a volume ratio of 9:1 to a concentration of about lot by weight, casted on a glass plate and dried at room temperature for removing the solvent to give a semi-transparent and colorless tough film having a thickness of 58 μm. The results of measurement for proton conductivity and the ion exchange capacity of the film are collectively shown in Table 1.

Example 6

A Block Copolymer Formed by Reacting a Disulfonylimide Oligomer Having Terminal Fluorine Groups and Composed of BSI 2 and Hydroquinone with a Polyether Sulfone Having Terminal Hydroxy Groups Into a flask were placed 0.500 g of BSI 2, 0.105 g of hydroquinone, 0.140 g of potassium carbonate and 4 ml of DMSO under nitrogen stream and they were heated with stirring at 80° C. for 15 hours. Then, 0.150 g of the polyether sulfone oligomer having terminal hydroxy groups similar to that in Example 3 was added and the reaction was continued at 80° C. for 24 hours. After completion of the reaction, the polymer was recovered in the same manner as that in Example 2 to give 0.57 g of a block copolymer having disulfonylimide blocks in the form of a brown solid. The results of measurement for molecular weight and 10% weight loss temperature are shown in Table 1.

The obtained polymer was converted into a film in the same manner as that in Example 1 to give a semi-transparent and pale brown tough film having a thickness of 26 μm. The results of measurement for proton conductivity and the ion exchange capacity of the film are collectively shown in Table 1.

Example 7

A Block Copolymer Formed by Reacting a Disulfonylimide Oligomer Having Terminal Fluorine Groups and Composed of BSI 2 and Hydroquinonesulfonic Acid with a Polyether Sulfone Having Terminal Hydroxy Groups Into a flask were placed 2.000 g of BSI 2, 0.780 g of potassium hydroquinonesulfonate, 0.563 g of potassium carbonate and 17 ml of DMSO under nitrogen stream and they were heated with stirring at 80° C. for 6 hours. Then, 3.352 g of the polyether sulfone oligomer having terminal hydroxy groups similar to that in Example 3 was added and the reaction was continued at 80° C. for 15 hours. After completion of the reaction, the polymer was recovered in the same manner as that in Example 2 to give 6.00 g of a block copolymer having disulfonylimide blocks in the form of a brown solid. The molecular weight is shown in Table 1.

The obtained polymer was converted into a film in the same manner as that in Example 5 to give a semi-transparent and pale brown tough film having a thickness of 27 μm. The results of measurement for proton conductivity and the ion exchange capacity of the film are collectively shown in Table 1.

Example 8

A Block Copolymer Formed by Reacting a Disulfonylimide Oligomer Having Terminal Fluorine Groups and Composed of BSI 2 and Hydroquinonesulfonic Acid with a Polyether Sulfone Having Terminal Hydroxy Groups Into a flask were placed 5.153 g of BSI 2, 1.940 g of potassium hydroquinonesulfonate, 1.559 g of potassium carbonate and 40 ml of DMSO under nitrogen stream and they were heated with stirring at 80° C. for 6 hours. Then, 10.800 g of the polyether sulfone oligomer having terminal hydroxy groups similar to that in Example 3 was added and the reaction was continued at 80° C. for 10 hours. After completion of the reaction, the polymer was recovered in the same manner as that in Example 2 to give 14.40 g of a block copolymer having disulfonylimide blocks in the form of a brown solid. The results of measurement for molecular weight and 10% weight loss temperature are shown in Table 1.

The obtained polymer was converted into a film in the same manner as that in Example 5 to give a semi-transparent and pale brown tough film having a thickness of 45 μm. The results of measurement for proton conductivity and the ton exchange capacity of the film are collectively shown in Table 1.

Example 9

A Polymer Electrolyte Membrane Comprising the Polymer Electrolyte Obtained in Example 8 Composited with a Polytetrafluoroethylene Porous Membrane The polymer obtained in Example 8 was dissolved in a mixed solvent of methylene chloride and methanol in a volume ratio of 9:1 to a concentration of about 15%, applied onto polytetrafluoroethylene porous membrane (membrane thickness: 15 μm, porosity: 90%, pore diameter: 3.0 μm) fixed on a glass plate and dried at room temperature for removing the solvent to give a semi-transparent and pale brown tough film having a thickness of 57 μm. The results of measurement for proton conductivity and the ion exchange capacity of the film are collectively shown in Table 1.

Comparative Example 1

Polycondensation was carried out with 4,4'-dihydroxydiphenylsulfone, 4,4'-dihydroxybiphenyl and 4,4'-dichlorodiphenylsulfone in a molar ratio of 7:3:10 in the co-existence of potassium carbonate in diphenylsulfone as a solvent at a temperature of 200 to 290° C. The obtained polymer was sulfonated with concentrated sulfuric acid to give a random copolymer in which a sulfonic acid group is introduced into the biphenyl unit.

The obtained polymer was converted into a film in the same manner as that in Example 1 to give a colorless and transparent tough film having a thickness of 42 μm. The results of measurement for proton conductivity and the ion exchange capacity of the film are collectively shown in Table 1.

TABLE 1

|  | 10% weight loss temperature | Molecular weight (Mn) | Ion exchange capacity | Proton conductivity |
|---|---|---|---|---|
| Example 1 | 356° C. | $1.0 \times 10^5$ | 1.3 meq/g | $3.5 \times 10^{-2}$ S/cm |
| Example 2 | 339 | $6.3 \times 10^4$ | 1.1 | $4.9 \times 10^{-2}$ |
| Example 3 | 334 | $7.6 \times 10^4$ | 1.2 | $3.2 \times 10^{-2}$ |
| Example 4 | 305 | $5.3 \times 10^4$ | 1.6 | $1.4 \times 10^{-1}$ |
| Example 5 | 363 | $1.2 \times 10^5$ | 1.2 | $4.2 \times 10^{-2}$ |
| Example 6 | 346 | $1.3 \times 10^5$ | 1.3 | $4.8 \times 10^{-2}$ |
| Example 7 | 324 | $7.6 \times 10^4$ | 1.2 | $1.2 \times 10^{-1}$ |
| Example 8 | 318 | $4.2 \times 10^4$ | 1.1 | $6.5 \times 10^{-2}$ |
| Example 9 | — | — | 1.0 | $8.8 \times 10^{-2}$ |

TABLE 1-continued

| | 10% weight loss temperature | Molecular weight (Mn) | Ion exchange capacity | Proton conductivity |
|---|---|---|---|---|
| Comparative example | 341 | $8.2 \times 10^4$ | 1.1 | $1.3 \times 10^{-2}$ |

Example 10

Evaluation of Properties of a Fuel Cell

The polymer electrolyte obtained in Example 9 was inserted between carbon cloths having coatings of platinum on carbon to give a membrane-electrodes assembly (MEA). The MEA was inserted between separators for fuel cell to form a fuel cell.

For activation of the fuel cell, humidified hydrogen was fed to one side and humidified air was fed to the other side of the cell. The properties of the fuel cell were measured while keeping the acting temperature at 80° C. The relationship between the electric current density and the cell voltage is shown in Table 2.

TABLE 2

| Electric current density (A/cm$^2$) | Voltage (V) |
|---|---|
| 0.00 | 0.96 |
| 0.50 | 0.61 |
| 1.00 | 0.40 |

The polymer electrolytes of the invention give films which are excellent in proton conductivity, thermal resistance and strength, and therefore are suitable to proton conductive membranes for fuel cells. In addition, they are soluble in solvents because they do not contain substantially a cross-linking structure, can be easily converted to films and are excellent recycling efficiency. Furthermore, when they are composited with porous membranes, they exhibit a high proton conductivity.

What is claimed is:

1. A polymer electrolyte having, in a main chain, a structural unit represented by the following formula (1):

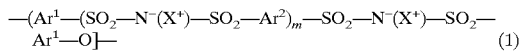

and further comprising, in a main chain, a structural unit represented by the following formula (2):

—[Ar$^3$—O]—      (2)

wherein Ar$^1$ and Ar$^2$ independently represent a divalent aromatic groups, m represents an integer of 0 to 3, X$^+$ represents an ion selected from hydrogen ion, an alkali metal ion and ammonium ion and Ar$^3$ represents a divalent aromatic group.

2. The polymer electrolyte according to claim 1, further having, in a main chain, a structural unit represented by the following formula (2') which is different from the formula (2):

—[Ar$^4$—O]—      (2')

wherein Ar$^4$ represents a divalent aromatic group.

3. A process for producing a polymer electrolyte according to claim 2 which comprises reacting a compound represented by the formula (3) shown below, an aromatic diol represented by the formula (4) shown below and a compound represented by the formula (5) shown below:

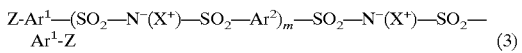

wherein Ar$^1$, Ar$^2$, Ar$^3$, Ar$^4$, m, X$^+$ and Z represent the same meanings as above; and W represents halogen or nitro.

4. The polymer electrolyte according to claim 1, wherein the divalent aromatic group is at least one group selected from the following structures:

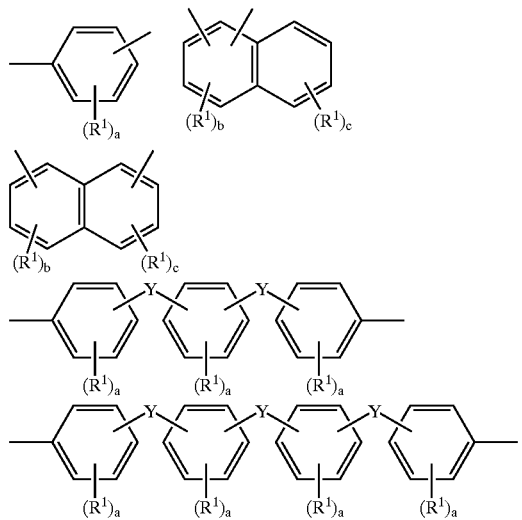

wherein R$^1$ represents alkyl having 1 to 10 carbon atoms, halogenated alkyl having 1 to 10 carbon atoms, aryl, acetyl, benzoyl, nitrile, sulfonic acid, carboxylic acid, phosphonic acid or halogen; a represents an integer of 0 to 4; b and c represent integers of 0 to 4, with the sum of b and c being an integer of 0 to 6; when a plurality of R$^1$s exist, they may be the same or different; Y represents a direct bond, —O—, —S—, —C(O)—, —SO$_2$— or —C(R$^3$)$_2$— wherein R$^3$ represents hydrogen, alkyl having 1 to 10 carbon atoms or halogenated alkyl having 1 to 10 carbon atoms, aryl, with the two R$^3$s being possible to be the same or different or to form a ring; and when a plurality of Ys exist, they may be the same or different.

5. The polymer electrolyte according to claim 1, wherein Ar$^1$ is tetrafluorophenylene.

6. The polymer electrolyte according to claim 1, wherein m is 0 or 1.

7. The polymer electrolyte according to claim 1, which is a block copolymer comprising a block having a structural unit represented by the formula (1) and a structural unit represented by the formula (2).

8. A polymer electrolyte membrane comprising a polymer electrolyte according to any one of claims 1 or 2 to 7.

9. A fuel cell comprising a polymer electrolyte membrane according to claim 8.

10. A polymer electrolyte membrane comprising a polymer electrolyte according to any one of claims 1 or 2 to 7 composited with a porous membrane.

11. The composite membrane according to claim 10, wherein the porous membrane comprises an aliphatic polymer or a fluorine-containing polymer.

12. The composite membrane according to claim 11, wherein the porous membrane comprises polytetrafluoroethylene.

13. A fuel cell comprising a polymer electrolyte membrane according to claim 12.

14. A fuel cell comprising a polymer electrolyte membrane according to claim 11.

15. A fuel cell comprising a polymer electrolyte membrane according to claim 10.

16. A process for producing a polymer electrolyte according to claim 1 which comprises polymerizing a compound represented by the formula (3) shown below with an aromatic diol represented by the formula (4) shown below:

$$Z\text{-}Ar^1\text{---}(SO_2\text{---}N^-(X^+)\text{---}SO_2\text{---}Ar^2)_m\text{---}SO_2\text{---}N^-(X^+)\text{---}SO_2\text{---}Ar^1\text{-}Z \quad (3)$$

$$HO\text{---}Ar^3\text{---}OH \quad (4)$$

wherein $Ar^1$, $Ar^2$, $Ar^3$, m and $X^+$ represent the same meanings as above; and Z represents halogen or nitro.

17. A process for producing a polymer electrolyte according to claim 1 which comprises polymerizing a compound represented by the formula (3) shown below with an aromatic diol represented by the formula (4) shown below, and then reacting a compound having hydroxyl represented by the formula (6) shown below:

$$Z\text{-}Ar^1\text{---}(SO_2\text{---}N^-(X^+)\text{---}SO_2\text{---}Ar^2)_m\text{---}SO_2\text{---}N^-(X^+)\text{---}SO_2\text{---}Ar^1\text{-}Z \quad (3)$$

$$HO\text{---}Ar^3\text{---}OH \quad (4)$$

$$HO\text{---}[Ar^5\text{---}O]_j\text{---}H \quad (6)$$

wherein $Ar^1$, $Ar^2$, $Ar^3$, m, $X^+$ and Z represent the same meanings as above; and $Ar^5$ represents a divalent aromatic group; and j represents an integer of 1 to 5000.

18. A process for producing a polymer electrolyte according to claim 1 which comprises polymerizing a compound represented by the formula (3) shown below with an aromatic diol represented by the formula (7) shown below, and then reacting a compound having hydroxyl represented by the formula (7) shown below:

$$Z\text{-}Ar^1\text{---}(SO_2\text{---}N^-(X^+)\text{---}SO_2\text{---}Ar^2)_m\text{---}SO_2\text{---}N^-(X^+)\text{---}SO_2\text{---}Ar^1\text{-}Z \quad (3)$$

$$HO\text{---}Ar^3\text{---}OH \quad (4)$$

$$W\text{---}[Ar^6\text{---}O]_j\text{---}Ar^6\text{---}W \quad (7)$$

wherein $Ar^1$, $Ar^2$, $Ar^3$, m, $X^+$, Z and j represent the same meanings as above; $Ar^6$ represents a divalent aromatic group; and W represents halogen or nitro.

19. A disulfonylimide compound represented by the following formula (3'):

$$Z\text{-}Ar^1\text{---}(SO_2\text{---}N^-(X^+)\text{---}SO_2\text{---}Ar^2)_n\text{---}SO_2\text{---}N^-(X^+)\text{---}SO_2\text{---}Ar^1\text{-}Z \quad (3)$$

wherein $Ar^1$, $Ar^2$, $X^+$ and Z represent the same meanings as above; and n represents an integer of 1 to 3.

20. The disulfonylimide compound according to claim 19, wherein n is 1.

21. The disulfonylimide compound according to claim 19, wherein n is 2 or 3.

22. A process for producing a disulfonylimide compound according to any one of claims 19 to 21 which comprises reacting a sulfonamide compound represented by the formula (8) shown below with a bissulfonyl chloride compound represented by the formula (9) shown below or reacting a sulfonyl chloride compound represented by the formula (10) shown below with a bissulfonamide compound represented by the formula (11) shown below, in the presence of a base:

$$Z\text{-}Ar^1\text{---}SO_2NH_2 \quad (8)$$

$$ClSO_2\text{---}Ar^2\text{---}SO_2Cl \quad (9)$$

$$Z\text{-}Ar^1\text{---}SO_2Cl \quad (10)$$

$$NH_2SO_2\text{---}Ar^2\text{---}SO_2NH_2 \quad (11)$$

wherein $Ar^1$, $Ar^2$ and Z represent the same meanings as above.

23. A process for producing a disulfonylimide compound according to claim 21 which comprises reacting a bissulfonyl chloride compound represented by the formula (9) shown below and a bissulfonamide compound represented by the formula (11) shown below with a sulfonyl chloride compound represented by the formula (8) shown below or a sulfonamide compound represented by the formula (10) shown below, in the presence of a base:

$$Z\text{-}Ar^1\text{---}SO_2NH_2 \quad (8)$$

$$ClSO_2\text{---}Ar^2\text{---}SO_2Cl \quad (9)$$

$$Z\text{-}Ar^1\text{---}SO_2Cl \quad (10)$$

$$NH_2SO_2\text{---}Ar^2\text{---}SO_2NH_2 \quad (11)$$

wherein $Ar^1$, $Ar^2$ and Z represent the same meanings as above.

* * * * *